(12) United States Patent
Ekdahl et al.

(10) Patent No.: US 6,806,947 B1
(45) Date of Patent: Oct. 19, 2004

(54) APPARATUS FOR MONITORING A FLUID CONDUIT

(75) Inventors: Olof Ekdahl, Lund (SE); Per-Ola Wictor, Stehag (SE)

(73) Assignee: Gambro AB (SE)

( * ) Notice: Subject to any disclaimer, the term of this patent is extended or adjusted under 35 U.S.C. 154(b) by 0 days.

(21) Appl. No.: 09/786,930

(22) PCT Filed: Sep. 6, 1999

(86) PCT No.: PCT/SE99/01541

§ 371 (c)(1),
(2), (4) Date: Jul. 5, 2001

(87) PCT Pub. No.: WO00/15278

PCT Pub. Date: Mar. 23, 2000

(30) Foreign Application Priority Data

Sep. 10, 1998 (SE) .................................. 9803055

(51) Int. Cl.[7] .................. G01N 21/85; A61M 1/36; A61M 5/36
(52) U.S. Cl. .................. 356/39; 356/339; 356/401; 356/614
(58) Field of Search .................. 356/39, 339, 401, 356/614

(56) References Cited

U.S. PATENT DOCUMENTS

| | | | |
|---|---|---|---|
| 3,998,551 A | 12/1976 | Suga | 356/73 |
| 4,366,384 A * | 12/1982 | Jensen | 250/575 |
| 4,681,563 A * | 7/1987 | Deckert et al. | 604/67 |
| 4,797,655 A * | 1/1989 | Orndal et al. | 340/521 |
| 4,830,194 A | 5/1989 | Kajiura et al. | 209/580 |
| 4,884,065 A * | 11/1989 | Crouse et al. | 340/632 |
| 5,319,182 A * | 6/1994 | Havens et al. | 235/462.42 |
| 5,644,402 A | 7/1997 | Chevallet | 356/440 |
| 5,680,111 A | 10/1997 | Danby et al. | 340/632 |
| 5,928,179 A * | 7/1999 | Plotkin | 604/6.1 |

FOREIGN PATENT DOCUMENTS

EP 0 238 809 B1 9/1987
EP 0 467 805 A1 1/1992

* cited by examiner

Primary Examiner—Constantine Hannaher
Assistant Examiner—Shun Lee
(74) Attorney, Agent, or Firm—Lerner, David, Littenberg, Krumholz & Mentlik, LLP (57) ABSTRACT

Apparatus and methods for determining the presence of a fluid conduit at a predetermined location and at least one characteristic of the fluid in the conduit are disclosed. The apparatus includes a light source for generating radiated light in a direction towards the predetermined location, such that when the fluid conduit is present at the predetermined location the radiated light passes in a direction through the fluid conduit, a first optical sensor for detecting the radiated light through the fluid conduit, and a second optical sensor for detecting the radiated light which is reflected by the fluid conduit.

20 Claims, 4 Drawing Sheets

APPARATUS FOR MONITORING A FLUID CONDUIT

FIELD OF THE INVENTION

The present invention relates to an apparatus for detecting the presence of a fluid conduit and at least one characteristic of the contents of the fluid conduit, the apparatus being disposed on a control device, for example, for the extracorporeal treatment of blood, with a light source, the radiation of which is directed towards the conduit and through the conduit, and with an optical sensor for the radiation emitted by the light source that detects the radiation directed through the fluid conduit.

The apparatus according to the present invention is intended for use with control devices for dialysis, which are also termed monitors. In this case, the fluid conduit may be filled with blood, a rinsing liquid or air.

BACKGROUND OF THE INVENTION

A number of apparatus are known for the purpose of monitoring a fluid conduit or tube that is connected to a dialysis monitor. For example, air detectors are known which check the blood in the fluid conduit that is passed back to the patient for the presence of air or air bubbles. Furthermore, blood detectors are known that check the dialysate liquid passed back by the dialyzer for the presence of blood, and thus are able to determine the presence of a leak in the dialyzer membrane. As soon as these detectors determine air or blood in the fluid passed through the conduit, a control unit of the monitor connected with the detectors sets off an alarm to prevent endangering the patient. Moreover, an alarm is set off when a fluid conduit is absent, provided that these detectors are also designed to monitor the fluid conduit.

Normally, these known devices include a photoelectric section that is arranged such that it passes through the essentially transparent fluid conduit. For example, apparatus is known from German Patent No. 37 68 033 in which the infrared light from a source is transmitted using a waveguide to a tube or to a recess in a tube support that is intended to hold the tube. The light is transmitted through a second light section from the recess to a receiver. Depending on whether a tube is mounted or not, and whether it contains essentially transparent rinsing liquid or blood, a varying amount of light reaches the receiver. This sends a signal to an evaluating device or control unit, the signal that is dependent on the amount of received light thereby providing information about the condition of the tube or the contents of the tube. When no tube is present, the light reaches the receiver unfiltered or unattenuated, and the receiver then sends a high signal to the control unit. If a tube is mounted and filled with air or colorless fluid, for example rinsing fluid, the light reaches the receiver slightly filtered or attenuated, and the receiver then delivers a medium signal to the control unit. If the tube is filled with blood the light will be essentially completely attenuated, and at most a small amount of light will reach the receiver, which then supplies the control unit with a low level signal.

A disadvantage of this type of apparatus is that with certain tubes, as a result of their shape and composition, a lens effect can arise that distorts the results. In the worst case, this can lead to the same amount of light being transmitted to the receiver when a mounted tube is filled with colorless fluid as when a tube is not mounted. In both cases the receiver generates an identical signal, so that no differentiation is possible between the two states.

An apparatus is known from European Patent No. 0 467 805 in which the light source and receiver are each arranged to protrude such that they deform the tube. In this manner, the astigmatic focusing, the so-called lens effect, which otherwise results from the cylindrical geometry and focuses the light beam onto the receiver, is obviated. However, with this apparatus only the nature of the fluid present in the tube is determined with the photoelectric section, while the presence of the tube is determined using an electromechanical sensor. As a result of this supplementary electromechanical sensor, the apparatus is complicated and therefore costly, and at the same time it is unreliable due to the additional possibility of error.

Another apparatus is known from U.S. Pat. No. 5,644,402 which detects both the presence of a tube and also the characteristics of the fluid transported in the tube, with a photoelectric section. To this end, the light source, the receiver and a number of deflectors are disposed in a complicated geometric arrangement such that, depending on whether the tube is present, and on its content and the resulting differing refraction, the light beam either does not reach the receiver at all, or is once or twice diffracted. It is indeed possible to determine with a photoelectric section whether a tube is present and what characteristics the content has, and it is also possible to achieve greater sensitivity as a result of the partially longer light path. However, on the whole, this apparatus is very complex and therefore expensive. In addition, it is highly subject to failure and must be precisely adjusted to the tube in question in order to be able to provide accurate information.

In view of this background it is therefore an object of the present invention to provide an apparatus of the type described in the introduction with which a reliable investigation of the presence of a fluid conduit and also at least one characteristic of the content of the fluid conduit is possible with little expense, to improve the safety of the patient.

SUMMARY OF THE INVENTION

In accordance with the present invention, this and other objects have now been realized by the invention of apparatus for determining the presence of a fluid conduit at a predetermined location and at least one characteristic of the contents of the fluid conduit, the apparatus comprising a light source for generating radiated light in a direction towards the predetermined location, whereby when the fluid conduit is present at the predetermined location the radiated light passes in a direction through the fluid conduit, a first optical sensor for detecting the radiated light passing through the fluid conduit, and a second optical sensor for detecting the radiated light which is reflected by the fluid conduit. In a preferred embodiment, the apparatus is in combination with a control device. Preferably, the control device comprises a device for the extracorporeal treatment of blood.

In accordance with one embodiment of the apparatus of the present invention, the second optical sensor is integrally formed with the light source.

In accordance with another embodiment of the apparatus of the present invention, the apparatus includes a housing, and the light source, the first optical sensor and the second optical sensor are disposed in the housing. Preferably, the apparatus is in combination with a control device. In a preferred embodiment, the housing constitutes a portion of the control device.

In accordance with another embodiment of the apparatus of the present invention, the apparatus includes a first waveguide for transmitting the radiated light from the light source to the predetermined location and for transmitting the radiated light reflected by the conduit to the second optical sensor, and a second waveguide for transmitting the radiated light which passes through the fluid conduit to the first optical sensor. In a preferred embodiment, the apparatus is in combination with a control device. Preferably, the apparatus includes a housing, and the light source, the first optical sensor, and the second optical sensor are disposed in the housing, and the apparatus includes a fluid conduit holder for holding the fluid conduit at the predetermined location, the fluid conduit holder disposed on the housing, the first and second waveguides being integrated with the fluid conduit holder.

In accordance with another embodiment of the apparatus of the present invention, the first waveguide is disposed at a location adjacent to the fluid conduit whereby an air gap is created therebetween. In a preferred embodiment, the light source generates the radiated light having a predetermined wavelength and a predetermined modulation. Preferably, the predetermined wavelength comprises a wavelength in the range of infrared radiation, and the predetermined modulation comprising a substantially square pulse sequence.

In accordance with another embodiment of the apparatus of the present invention, the control device includes a control unit, and the first and second optical sensors are electrically connected to the control unit, the first optical sensor providing a first signal and the second optical sensor providing a second signal.

In a preferred embodiment, the control device includes comparing means for comparing the first and second signals with predetermined signal values, whereby when the first signal is at a predetermined high level and the second signal is at a predetermined low level, the comparing means determines that the fluid conduit is not present at the predetermined location, when the first signal is at a predetermined medium level and the second signal is at a predetermined high level, the comparing means determines that the fluid conduit is present at the predetermined location and the fluid is not present in the fluid conduit, when the first signal is at a predetermined high level and the second signal is at a predetermined high level, the comparing means determines that the fluid conduit is present at the predetermined location and the fluid comprises a transparent fluid, when the first signal is at a predetermined low level and the second signal is at a predetermined high level, the comparing means determines that the fluid conduit is present at the predetermined location and the fluid comprises an opaque fluid, when the first signal is at a predetermined low level and pulses at a predetermined high level, and the second signal is at a predetermined high level, the comparing means determines that the fluid conduit is present at the predetermined location and the fluid comprises an opaque fluid containing air bubbles, and when the first signal is at a predetermined low or medium level and the second signal is at a predetermined low level, the comparing means determines that an error condition exists.

In accordance with a preferred embodiment of the apparatus of the present invention, the control device comprises a dialysis monitor.

In accordance with the present invention, a method has been devised for determining the presence of a fluid conduit at a predetermined location and at least one characteristic of the contents of the fluid conduit, the method comprising directing radiated light towards the predetermined location whereby when the fluid conduit is present at the predetermined location the radiated light passes in a direction through the conduit, detecting a first portion of the radiated light passing through the fluid conduit and detecting a second portion of the radiated light which is reflected by the fluid conduit. In accordance with a preferred embodiment, the method includes comparing the first and second portions of the radiated light with predetermined values therefor whereby when the first portion of the radiated light is at a predetermined high level and the second portion of the radiated light is at a predetermined low level, determining that the fluid conduit is not present at the predetermined location, when the first portion of the radiated light is at a predetermined medium level and the second portion of the radiated light is at a predetermined high level, determining that the fluid conduit is present at the predetermined location and the fluid is not present in the fluid conduit, when the first portion of the radiated light is at a predetermined high level and the second portion of the radiated light is at a predetermined high level, determining that the fluid conduit is present at the predetermined location and the fluid comprises a transparent fluid, when the first portion of the radiated light is at a predetermined low level and the second portion of the radiated light is at a predetermined high level, determining that the fluid conduit is present at the predetermined location and the fluid comprises an opaque fluid, when the first portion of the radiated light is at a predetermined low level and pulses at a predetermined high level, and the second portion of the radiated light is at a predetermined high level, determining that the fluid conduit is present at the predetermined location and the fluid comprises an opaque fluid including air bubbles, and when the first portion of the radiated light is at a predetermined low or medium level and the second portion of the radiated light is at a predetermined low level, determining that an error condition exists.

The objects of the present invention are achieved with an apparatus of the nature of that described above, that also includes a second optical sensor which detects the radiation reflected from the fluid conduit.

In this manner, a simply constructed apparatus is provided with which, inter alia, the presence of a fluid conduit or tube can be reliably ascertained. If a fluid conduit is present, the light beam directed towards the fluid conduit by the light source will be partially reflected, this reflection being detected by the second optical sensor. The latter then generates a signal at a high level that is transmitted to a control unit, for example, of a monitor, where it is processed. If no fluid conduit is present then no light can be reflected from the fluid conduit onto the second optical sensor, so that this will generate no signal, or only a signal of low level, and transmit this signal to the control unit. In this manner, the presence of a fluid conduit can be reliably determined solely by means of the signal from the second optical sensor.

The unreflected light beam, or the unreflected portion of the light beam, is detected by the first optical sensor, which generates a signal dependent on the intensity of the received light radiation and passes this signal on to the control unit. If no fluid conduit is present, the entire light radiation reaches the first optical sensor unreflected and unfiltered or unattenuated and not weakened, the latter then generates a signal at a high level, and sends this signal to the control unit. A high-level signal can likewise be generated when a fluid conduit is mounted and contains a transparent liquid, as was described in detail above with reference to the lens effect. However, since a second signal is available from the fluid conduit, this signal allows the described condition of fluid conduit with transparent fluid to be assigned without ambiguity. The previously existing difficulties in distinguishing these two conditions are thus easily and reliably overcome.

The other characteristics of the fluid conducted through the fluid conduit may also be determined in a simple manner. If the fluid conduit is present and filled only with air, the light beam will be somewhat attenuated, so that a reduced portion will be detected by the first optical sensor. This then generates a signal of medium level, and passes this signal on to the control unit. If a fluid conduit is present and filled with blood, the light radiation will be essentially completely filtered, and at the most, only a small portion of the light radiation will arrive at the first optical sensor. This then generates a low-level signal and sends this signal to the control unit.

Finally, the presence of air bubbles in a fluid conduit filled with blood can also be easily ascertained. In contrast to the surrounding blood, air bubbles essentially do not attenuate the light beam, so that a substantially unfiltered light beam will pass through the blood containing air bubbles and arrive at the first optical sensor. Thus, when blood containing air bubbles flows past and momentarily allows the light beam to arrive at the first optical sensor substantially unfiltered, the latter generates a short, high-level impulse-like signal, which is superimposed on the low-level signal indicating blood. The presence of air bubbles in the blood can thus be determined simply from the signal shaped from the first optical sensor: a low-level base signal on which are superimposed high-level impulses. In this manner, a simple measurement of air bubbles is enabled, independent of the type of tube and its position, simply by detecting peaks or impulses on the existing base signal.

Error conditions may also be determined with the apparatus according to the present invention, e.g. the presence of an incorrect fluid conduit, or that the light of the light source is too weak, or the light source or the first and/or second sensor is/are faulty. In such cases the first sensor generates a signal of low or medium level and the second sensor generates a signal of low level.

Accordingly, with the apparatus according to the present invention the presence of a fluid conduit, at least one characteristic of the content of the fluid conduit, and error conditions can be determined easily and reliably as is summarized in the following table.

TABLE

| | Signal from the first sensor | Signal from the second sensor |
|---|---|---|
| No fluid conduit | high level | low level |
| Fluid conduit present, but empty | medium level | high level |
| Fluid conduit present, filled with transparent fluid | high level | high level |
| Fluid conduit present, filled with blood | low level | high level |
| Fluid conduit present, filled with blood, air bubbles | low level with high-level impulses | high level |
| Error conditions | low or medium level | low level |

Error conditions could, for example, be: light source too weak, first and/or second sensor faulty, and incorrect fluid conduit.

It should be noted that when using sensors that, for example, give a low-level signal with a strong received light beam and a high level signal with a weak received light beam, the above table is correspondingly reversed. Such an arrangement of the apparatus operating in a kinematically reversed manner is likewise incorporated herein.

The apparatus according to the present invention can be further simplified when, in accordance with a preferred embodiment of the present invention, the second optical sensor is combined with the light source and, for example, is formed integrally with the light source. The use of such a reflection sensor reduces the number of individual components required for the apparatus, whereby the complexity of the apparatus, and consequently the risk of failure, is further reduced.

It should be noted at this point that this is only a preferred embodiment, and that the second optical sensor may be arranged as desired independent of the light source, provided that it captures the light reflected from the fluid conduit. Any desired sensor can be used as an optical sensor, for example, phototransistors, photodiodes or photoresistors.

According to a further preferred embodiment, at least the sensitive electrical and electronic components of the apparatus are integrated in the monitor housing, so that they are protected from external influences, and safety is increased. External influences may, for example, constitute moisture, water and glucose or coffee, as well as electromagnetic radiation. Coffee out of a cup that has been placed on the monitor and is knocked over could, for example, run down the monitor and the apparatus, or glucose could accidentally drop on the monitor or be squirted against the apparatus when being administered to a dialysis patient. Electromagnetic radiation can cause disruption of the signal transmission from the sensors to the monitor device.

In order to ensure the safe transmission of radiation transmitted from the light source towards the fluid conduit, as well as a safe transmission towards the first optical sensor, it is advantageous to provide, in accordance with another embodiment, a first waveguide that guides the light or the radiation from the light source to the fluid conduit and the reflected light from the fluid conduit to the second sensor, and a second waveguide that guides light directed towards the fluid conduit to the first optical sensor after it has passed through the fluid conduit. In this manner, a defined light path is created that ensures the safe operation of the apparatus irrespective of random external influences.

The waveguides may be made of any desired light— conducting material, such as quartz glass, and may also be formed freely with respect to diameter. However, it is advantageous to form the diameter such that it is smaller than the diameter of the fluid conduit to be detected. This creates the advantage that all the emitted light is utilized for detecting the fluid conduit or its content, and consequently higher precision and efficiency are achieved.

However, instead of using waveguides, it is also possible to create a defined light path using mirrors, for example as is disclosed in German Patent No. 37 68 033.

According to an alternative embodiment, the first and second waveguides are integrated in a conduit holder or tube holder that is arranged on the monitor housing. In this manner, a defined relative association between the fluid conduit and sensors is enabled which further improves the precision and reliability of the measurement.

In this arrangement, the waveguide guiding the light from the light source to the fluid conduit can also be arranged such that it touches the fluid conduit. However, it can also be arranged such that an air gap is present between the end of the waveguide and the fluid conduit. This is particularly necessary when the refractive indexes of the adjacently arranged materials are so similar that either no, or only insufficient, reflection is obtained. By providing an air gap, a sufficient difference between the refractive indexes of the adjacently disposed materials, and hence a sufficient reflection of the light beam at the mounted fluid conduit, is obtained.

The light emitted from the light source can be unmodulated light of any desired wavelength. However, it is advantageous when the emitted light is modulated to allow reliable detection of light transmitted by the light source and reflected from, or transmitted through, the fluid conduit, irrespective of the surrounding light. For example, light with a wavelength of between about 880 and 890 nm and a modulation frequency of about 10 kHz may be used. The isolation from surrounding light can be implemented simply by filtering the modulation out of the signal at the detector.

Preferably, light in the infrared region is transmitted and modulated, for example, with a square wave pulse sequence, since components for this arrangement are known, and the work and cost involved in the apparatus will be reduced.

It should also be noted at this stage that when utilizing waveguides of glass material, light with a wavelength below about 350 nm should not be used, as such short wavelengths are absorbed by glass.

BRIEF DESCRIPTION OF THE DRAWINGS

The present invention will now be described in more detail with reference to the following detailed description, which, in turn, refers to the accompanying drawings, in which.

DETAILED DESCRIPTION

Figure 1:
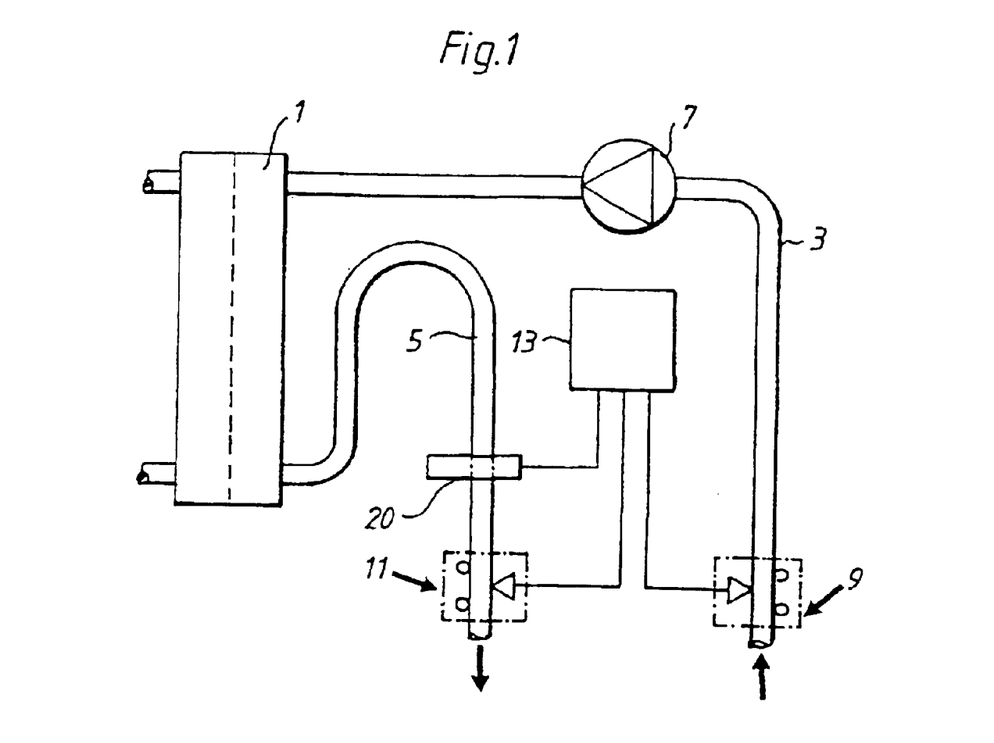
FIG. 1 is a top, elevational, schematic representation of a portion of a dialysis monitor with an apparatus according to the present invention arranged therein.

In the interest of improved clarity only some parts of a dialysis monitor, in which the apparatus according to the present invention is utilized, are depicted schematically in FIG. 1.

Blood from a patient is sent to a dialyzer 1 through an extracorporeal blood circuit by means of an arterial tube 3, the blood being moved to the dialyzer 1 in the tube 3 by means of a blood pump 7. The tube 3 can be clamped with an arterial clamp 9 that is activated by the control unit 13 of the monitor, which is not shown. The clamp 9 may, for example, be formed as an electromagnetically operable clamp and be operated by the control unit 13 of the monitor in case of alarm, in order to pinch off the tube, and consequently to prevent further blood from being taken from the patient.

The blood that is passed through the dialyzer 1 and cleaned there is sent back to the patient through a venous tube 5. An electromagnetically operable venous clamp 11, that is controlled in the same way by the control unit 13 of the monitor, is likewise disposed on the tube 5.

A detector 20 is arranged upstream of the clamp 11 in the direction of flow, and is also connected to the control unit 13 of the monitor. This detector 20 determines, on the one hand, the presence of the tube 5, and on the other, the characteristic of the content of the tube 5. If, for example, the detector 20 ascertains that the tube 5 contains rinsing liquid, or that air bubbles are contained in the blood being sent back to the patient, an alarm is generated by the control unit 13 of the monitor and the clamps 9 and 11 are activated to pinch off the tubes 3 and 5, respectively. In this manner, any danger to the patient is obviated and the patient's safety is improved.

The arrangement of the detector 20 depicted in the drawings is only an illustrative example. It is not intended to limit utilization of the detector to the arrangement described here within a dialysis monitor, nor to its use only in a dialysis monitor, or only in an extracorporeal blood circuit. For example, in addition to its utilization in hemodialysis, hemodiafiltration and hemofiltration, the apparatus can be employed inter alia during plasmapheresis, intravenous infusion, the exchange of blood components or the oxygenation during heart operations.

Figure 2:
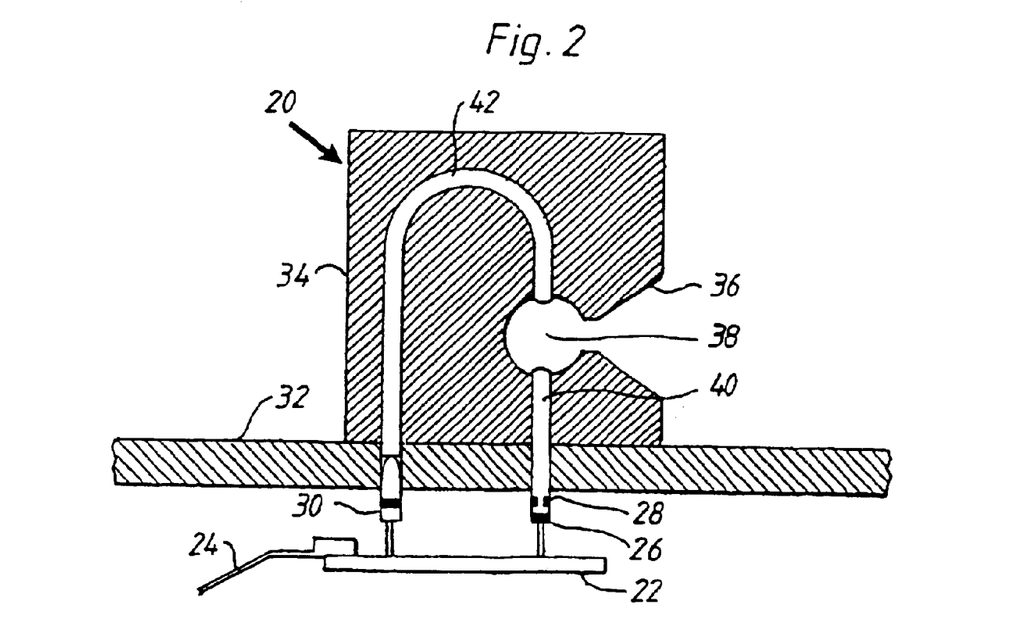
FIG. 2 is a side, elevational, cross-sectional, schematic view of a preferred embodiment of the apparatus of the present invention.

In FIG. 2, a preferred embodiment of the detector 20 is schematically shown in section. The detector 20 comprises a circuit board 22 on which the electrical components and circuits are arranged, and which is connected by an electrical connection 24 to the control unit 13 (FIG. 1) of the monitor, that is illustrated only by its housing 32. The circuit board 22 with its electrical components and circuits is disposed inside the housing 32 for protection. A light emitting diode (LED) 26 is provided as a light source on the circuit board 22. The LED 26 is combined with a phototransistor 28 and a waveguide 40, this arrangement forming the aforementioned reflection sensor. Furthermore, a sensor 30 that is responsive to the light emitted by the LED 26 is arranged on the circuit board 22.

The detector 20 further comprises a tube or conduit holder 34 that is arranged on the outside of the monitor housing 32 and can hold a tube that is not shown. The conduit holder 34 comprises a recess 36 that tapers inwardly and then opens up to an essentially cylindrical enlargement 38. This enlargement 38 receives the tube that is not shown and holds this in the conduit holder 34. The waveguide 40 connected to the LED 26 and the phototransistor 28 is guided by the monitor housing 32 and the conduit holder 34 up to the enlargement 38, so that light emitted from the LED 26 is guided towards the enlargement 38. A second waveguide 42 is likewise provided in the conduit holder 34 and arranged therein such that one end is directed towards the enlargement 38, and the other towards the sensor 30. To this end, corresponding openings are provided in both the monitor housing 32 and the conduit holder 34. At the same time, the end of the waveguide 42 directed towards the enlargement 38 is arranged to oppose the first waveguide 40. In this manner, the second waveguide 42 can receive the light transmitted towards the enlargement 38 by the first waveguide, and pass this light on to the sensor 30.

Figure 3:
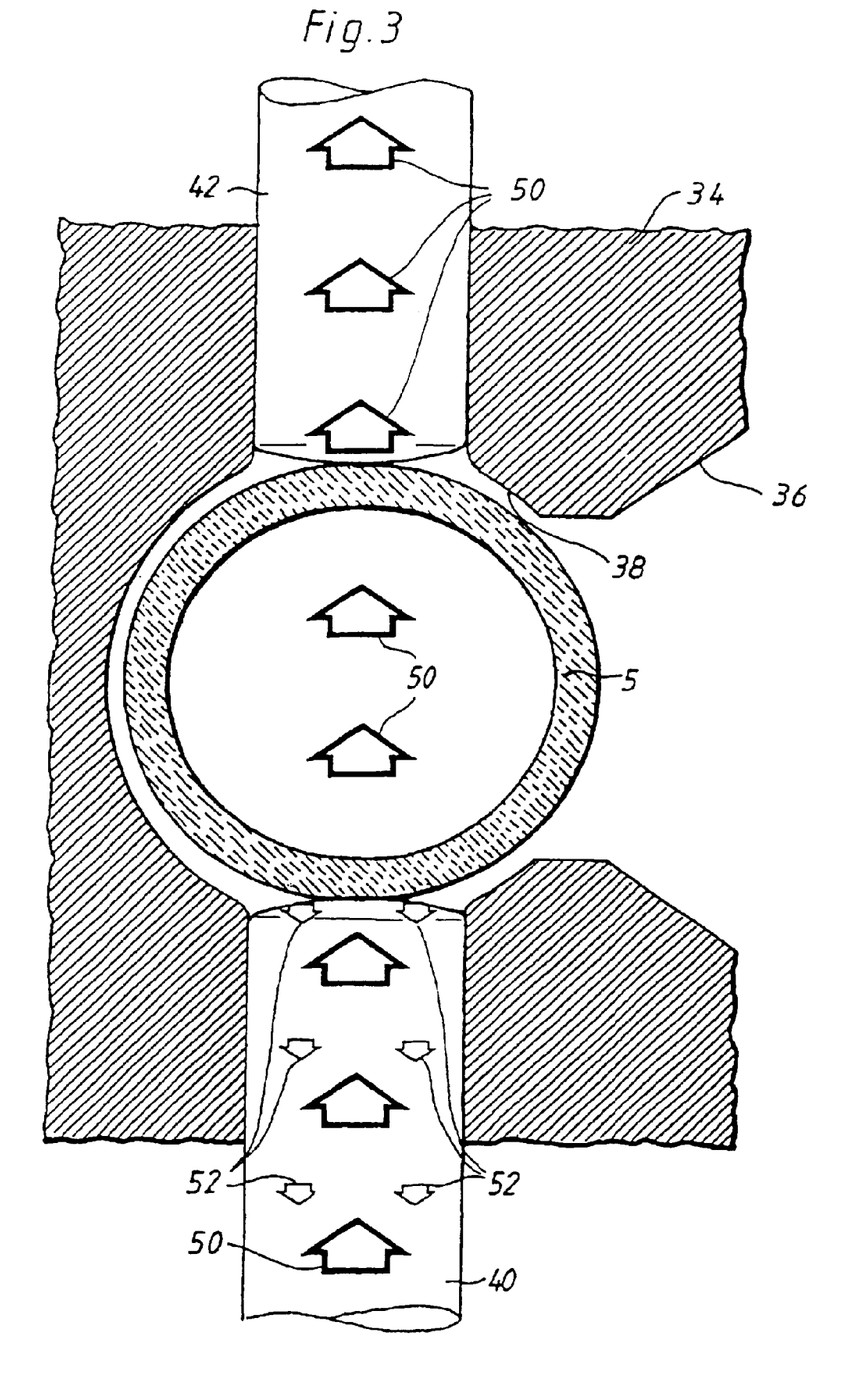
FIG. 3 is a partial, side, elevational, enlarged schematic view of light radiation in the apparatus according to FIG. 2.

This is schematically illustrated in FIG. 3. FIG. 3 shows the enlargement 38 of the conduit holder 34 in section, with a tube 5 that has been inserted through recess 36 of the enlargement. The light rays 50 transmitted by the light source, which is not shown here, are transmitted through the first waveguide 40 to the enlargement 38 and the tube 5 located therein. A portion of the light rays 50 will be reflected at the tube 5, as is illustrated by arrow 52. These light rays 52 will be detected by the phototransistor 28, which is also not shown here and which then generates a signal and sends this signal to the control unit of the monitor, both of which are not shown here. This signal simply and reliably indicates that a tube 5 is located in the conduit holder 34, as has been described in detail above.

A portion of the light rays 50 will be transmitted through the transparent tube 5 and will reach the second waveguide 42 arranged opposite thereto. This guides the light rays 50 further to the sensor 30 (FIG. 2), which generates a signal dependent on the intensity of the received light radiation 50 and passes this signal on to the control unit of the monitor. This signal simply and reliably indicates the characteristic of the fluid contained in the tube 5. As described above in detail, with this arrangement, the safe and reliable determination of whether the tube 5 is filled with air, with rinsing liquid or with blood, and whether the blood possibly contains air bubbles is enabled.

The arrangement depicted here in which the first waveguide 40 touches the tube 5 is only one embodiment of the apparatus according to the present invention. It is also possible to arrange the first waveguide 40 such that it is spaced from the tube 5 located in the enlargement 38.

Figure 4:
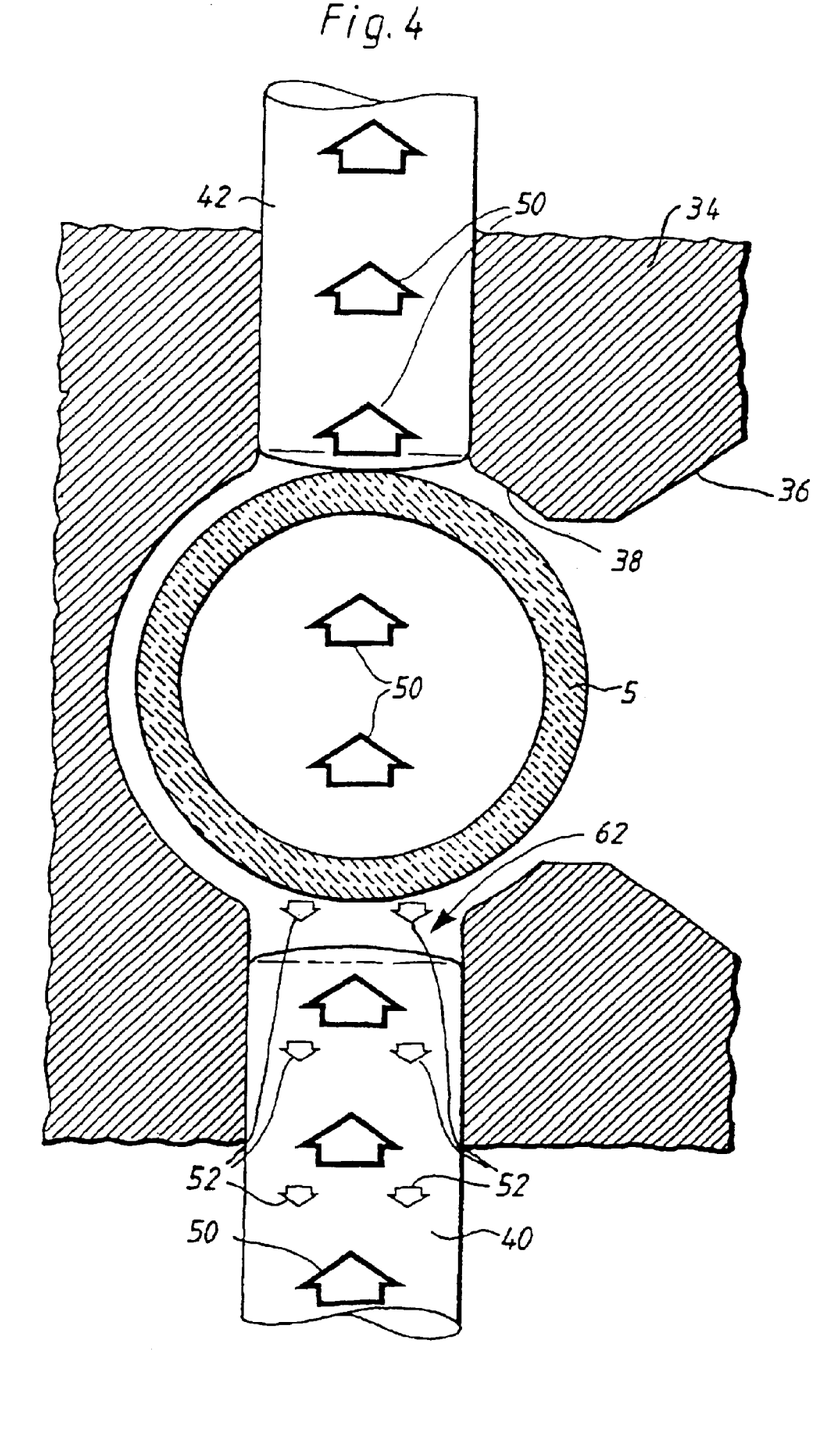
FIG. 4 is a partial, side, elevational, enlarged schematic view of light radiation according to a further preferred embodiment of the apparatus of the present invention.

This is shown in FIG. 4. In this embodiment, an air gap 62 is present between the tube 5 and the end of the waveguide 40 directed towards the recess 38 when a tube 5 is inserted in the conduit holder 34. This embodiment differs from that shown in FIG. 3 only in the air gap 62. Like parts are denoted by like reference numerals, so that no renewed detailed description as necessary here.

The air gap 62 can, for example, be implemented using spacers which are not shown in the drawing and which hold the tube at a certain distance from the waveguide 40 to form the illustrated air gap 62. It is also possible that the waveguide 40 comprises one or more recesses at its end directed towards the tube 5, so that the tube 5 lies against the projecting parts of the waveguide 40, while an air gap is formed between the recesses in the waveguide 40 and the tube 5.

The thus formed air gap may be necessary for certain materials or with a certain surface characteristic or shape of the tube 5 to ensure sufficient reflection of the light rays, that is dependent on the refractive indexes of the adjacently arranged materials in the direction of the light ray 50.

Figure 5:
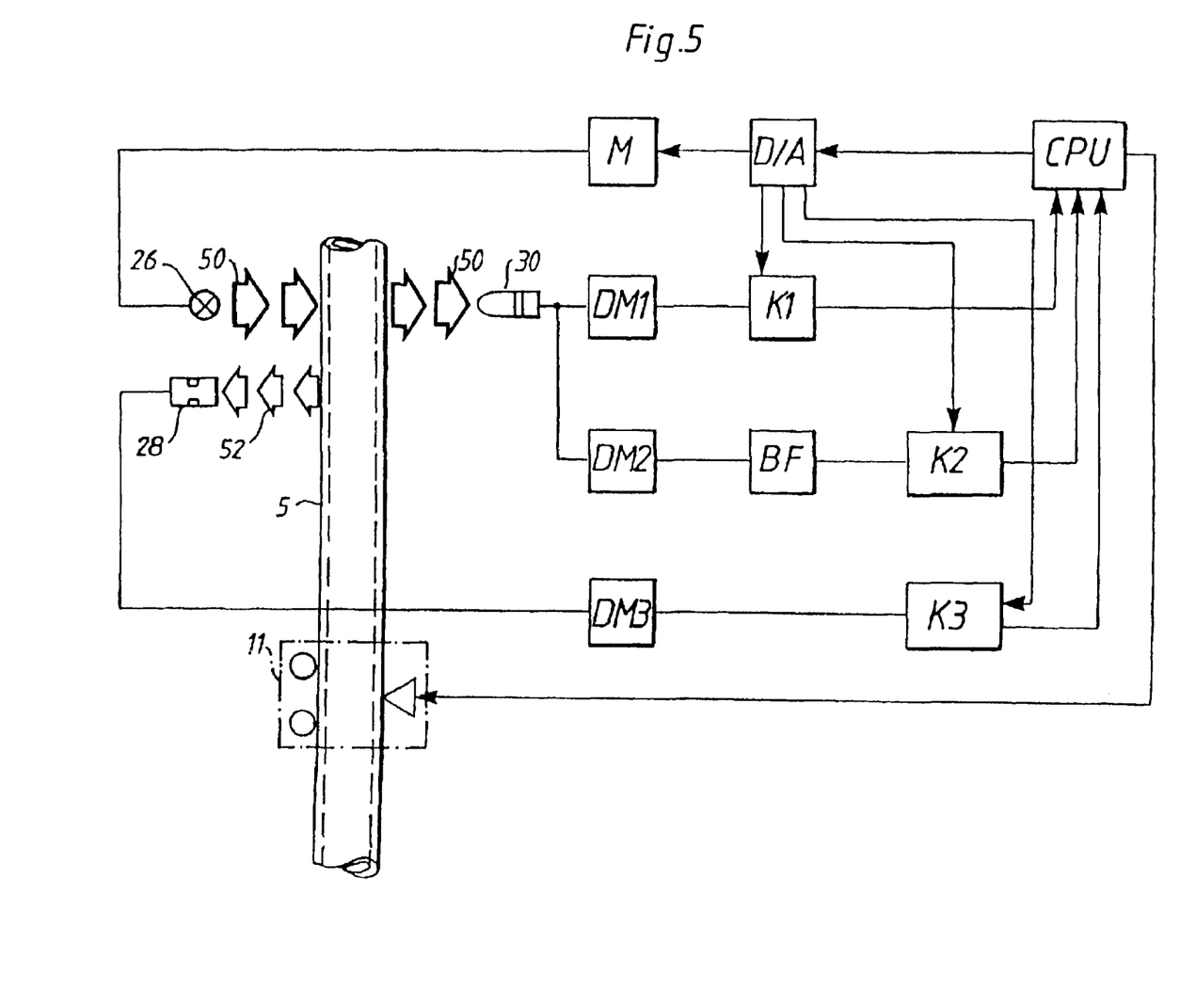
FIG. 5 is a top, elevational, schematic view of signal processing in the control unit according to the present invention.

FIG. 5 schematically shows a portion of the control unit 13 and parts of the venous tube 5 with the fitted venous clamp 11 and the photoelectric section of the apparatus according to the present invention. The tube 5 may be formed totally, or in the region of the photoelectric section, with a cylindrical or even an oval cross section, and may be composed of PVC or another conventional, transparent material used in the medical field. However, it is also possible that the tube be formed as a cell, for example of glass, with a rectangular cross section. The photoelectric section has already been described in detail with reference to FIG. 2, so that a renewed explanation is not necessary. The photoelectric section is shown schematically here, without the waveguide, only with the light source 26, the phototransistor 28 and the first sensor 30. The light source 26 sends light rays 50 towards the tube 5, which are transmitted through the transparently formed tube 5 and are detected by the first sensor 30. A portion of the light rays 50, denoted by 52, are reflected by the tube 5 and detected by the second sensor, the phototransistor 28.

The illustrated portion of the control unit 13 comprises a CPU, a D/A converter, a modulator M, three demodulators DM1, DM2 and DM3, a bandpass filter BF and three comparators, K1, K2 and K3. The CPU controls the modulator M that modulates the LED control current by means of the D/A converter. This has the effect that the light source 26 emits light rays 50 with a predetermined modulation, as described in detail above.

The modulated light rays 50 passing through the tube 5 are detected by the first sensor 30. This sensor then emits a signal which is demodulated by the demodulator DM1. In this manner, the influence of the surrounding light on the measurement in the photoelectric section is substantially excluded. The demodulated signal is then passed to the comparator K1, where it is compared with a predetermined value. This predetermined value is supplied from the CPU by means of the D/A converter to the comparator K1. It should be noted at this point that one embodiment only is being described here, and the predetermined value, the so-called "trigger value", could also be fed to the comparator in another manner.

If the signal supplied to the comparator K1 by the demodulator DM1 lies above this predetermined value, then either no tube 5 is present, or the tube is present and filled with transparent fluid, so that the same amount of light reaches the first sensor 30 as when the tube 5 is absent as a result of the lens effect described in detail above.

To differentiate between these two situations the CPU uses the signal delivered by the second sensor 28. This responds to the light rays 52 reflected by the tube 5, and emits a signal that is demodulated by the demodulator DM3 and then sent to a comparator K3. This comparator K3 compares the signal delivered by the sensor 28 with a predetermined value, which is supplied by the CPU by means of the D/A converter. If the signal lies below this value, then no tube 5 is present that could reflect light to the sensor 28. If the signal lies above the predetermined value, then a tube 5 is present, and light 52 is reflected towards the sensor 28, which then emits a signal at a high level. Thus, the CPU can decide with the help of the comparators K1 and K3 whether no tube 5 is present, or whether a tube is present that contains a transparent fluid.

In the same manner, the CPU can determine whether the tube 5 is filled with blood or is empty. To this end, the signal sent to the comparator K1 is compared with a second, low predetermined value. If the signal lies below this value, blood is present in the tube 5. In this case the light ray 50 will be substantially completely filtered, so that the sensor 30 supplies only a correspondingly low signal. If the tube is present, but empty, i.e. filled with air, the light rays 50 will be somewhat filtered and a corresponding signal will be sent by the sensor 30 to the comparator K1. If this signal lies below the first predetermined value and above the second predetermined value, then an empty tube is present. Hence, with the aid of the comparator K1, the CPU can also determine if an empty tube is present.

Finally, with the help of the comparator K2 the CPU can determine whether air bubbles are present in the fluid flowing through the tube 5. If, for example, air bubbles are present in blood flowing through the tube 5, then as these bubbles pass the photoelectric section they will allow the light rays 50 to reach the sensor 30 unhindered to a greater or lesser extent, depending on their size. The latter then generates a pulse-like signal corresponding to the passing bubbles. This signal emitted by the sensor 30 is sent both to the comparator K1, as described in detail above, and to the comparator K2 by means of the demodulator DM2 and the bandpass filter BF. The comparator K2 compares the signal with a predetermined value, and air bubbles are present when the signal lies above this value. In this case the CPU controls, for example, the venous clamp 11, which closes the tube 5. In this manner, any danger to the patient is prevented.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Apparatus for determining the presence of a fluid conduit having an exterior surface comprising:
    a light source disposed for generating radiated light in a direction towards a predetermined location, whereby when said fluid conduit is present at said predetermined location said radiated light passes in a direction through said fluid conduit;
    a first optical sensor for detecting a first portion of said radiated light passing through said fluid conduit; and
    a second optical sensor disposed for detecting a second portion of said radiated light, which is reflected by said exterior surface of said fluid conduit.

2. The apparatus of claim 1 in combination with a control device.

3. The apparatus of claim 2 wherein said control device comprises a device for the extracorporeal treatment of blood.

4. The apparatus of claim 2 wherein said control device includes a control unit, and wherein said first and second optical sensors are electrically connected to said control unit, said first optical sensor providing a first signal and said second optical sensor providing a second signal.

5. The apparatus of claim 4 wherein said control device includes comparing means for comparing said first and second signals with predetermined signal values, whereby:
    when said first signal is at a predetermined high level and said second signal is at a predetermined low level, said comparing means determines that said fluid conduit is not present at said predetermined location;
    when said first signal is at a predetermined medium level and said second signal is at a predetermined high level, said comparing means determines that said fluid conduit is present at said predetermined location and said fluid is not present in said fluid conduit;
    when said first signal is at a predetermined high level and said second signal is at a predetermined high level, said comparing means determines that said fluid conduit is present at said predetermined location and said fluid comprises a transparent fluid;
    when said first signal is at a predetermined low level and said second signal is at a predetermined high level, said comparing means determines that said fluid conduit is present at said predetermined location and said fluid comprises an opaque fluid;
    when said first signal is at a predetermined low level and pulses at a predetermined high level, and said second signal is at a predetermined high level, said comparing means determines that said fluid conduit is present at said predetermined location and said fluid comprises an opaque fluid containing air bubbles; and
    when said first signal is at a predetermined low or medium level and said second signal is at a predetermined low level, said comparing means determines that an error condition exists.

6. The apparatus of claim 2 wherein said control device comprises a dialysis monitor.

7. The apparatus of claim 1 wherein said second optical sensor is integrally formed with said light source.

8. The apparatus of claim 1 including a housing, and wherein said light source, said first optical sensor and said second optical sensor are disposed in said housing.

9. The apparatus of claim 8 in combination with a control device.

10. The apparatus of claim 9 wherein said housing constitutes a portion of said control device.

11. The apparatus of claim 1 including a first waveguide for transmitting said radiated light from said light source to said predetermined location and for transmitting said radiated light reflected by said conduit to said second optical sensor, and a second waveguide for transmitting said radiated light which passes through said fluid conduit to said first optical sensor.

12. The apparatus of claim 11 in combination with a control device.

13. The apparatus of claim 12 including a housing, and wherein said light source, said first optical sensor, and said second optical sensor are disposed in said housing, and including a fluid conduit holder for holding said fluid conduit at said predetermined location, said fluid conduit holder disposed on said housing, said first and second waveguides being integrated with said fluid conduit holder.

14. The apparatus of claim 12 wherein said first waveguide is disposed at a location adjacent to said fluid conduit whereby an air gap is created therebetween.

15. The apparatus of claim 1 wherein said light source generates said radiated light having a predetermined wavelength and a predetermined modulation.

16. The apparatus of claim 15 wherein said predetermined wavelength comprises a wavelength in the range of infrared radiation, and wherein said predetermined modulation comprising a substantially square pulse sequence.

17. A method for determining the presence of a fluid conduit at a predetermined location and at least one characteristic of said contents of said fluid conduit, said method comprising directing radiated light towards said predetermined location whereby when said fluid conduit is present at said predetermined location, said radiated light passes in a direction through said conduit, detecting a first portion of said radiated light passing through said fluid conduit and detecting a second portion of said radiated light which is reflected by an exterior surface of said fluid conduit.

18. The method of claim 17 including comparing said first and second portions of said radiated light with predetermined values therefor whereby:
    when said first portion of said radiated light is at a predetermined high level and said second portion of said radiated light is at a predetermined low level, determining that said fluid conduit is not present at said predetermined location;
    when said first portion of said radiated light is at a predetermined medium level and said second portion of said radiated light is at a predetermined high level, determining that said fluid conduit is present at said predetermined location and said fluid is not present in said fluid conduit;
    when said first portion of said radiated light is at a predetermined high level and said second portion of said radiated light is at a predetermined high level, determining that said fluid conduit is present at said predetermined location and said fluid comprises a transparent fluid;

when said first portion of said radiated light is at a predetermined low level and said second portion of said radiated light is at a predetermined high level, determining that said fluid conduit is present at said predetermined location and said fluid comprises an opaque fluid;

when said first portion of said radiated light is at a predetermined low level and pulses at a predetermined high level, and said second portion of said radiated light is at a predetermined high level, determining that said fluid conduit is present at said predetermined location and said fluid comprises an opaque fluid including air bubbles; and when said first portion of said radiated light is at a predetermined low or medium level and said second portion of said radiated light is at a predetermined low level, determining that an error condition exists.

19. A method for determining the presence of a fluid conduit with an exterior surface at a predetermined location and at least one characteristic of said contents of said fluid conduit, said method comprising:

directing radiated light towards said predetermined location whereby when said fluid conduit is present at said predetermined location said radiated light passes in a direction through said conduit;

detecting a first portion of said radiated light passing through said fluid conduit and detecting a second portion of said radiated light which is reflected by said exterior surface of said fluid conduit;

comparing said first and second portions of said radiated light with predetermined values therefor whereby:

when said first portion of said radiated light is at a predetermined high level and said second portion of said radiated light is at a predetermined low level, determining that said fluid conduit is not present at said predetermined location;

when said first portion of said radiated light is at a predetermined medium level and said second portion of said radiated light is at a predetermined high level, determining that said fluid conduit is present at said predetermined location and said fluid is not present in said fluid conduit;

when said first portion of said radiated light is at a predetermined high level and said second portion of said radiated light is at a predetermined high level, determining that said fluid conduit is present at said predetermined location and said fluid comprises a transparent fluid;

when said first portion of said radiated light is at a predetermined low level and said second portion of said radiated light is at a predetermined high level, determining that said fluid conduit is present at said predetermined location and said fluid comprises an opaque fluid;

when said first portion of said radiated light is at a predetermined low level and pulses at a predetermined high level, and said second portion of said radiated light is at a predetermined high level, determining that said fluid conduit is present at said predetermined location and said fluid comprises an opaque fluid including air bubbles; and when said first portion of said radiated light is at a predetermined low or medium level and said second portion of said radiated light is at a predetermined low level, determining that an error condition exists.

20. A method for determining the presence of a fluid conduit with an exterior surface at a predetermined location, said method comprising:

directing radiated light towards said predetermined location whereby when said fluid conduit is present at said predetermined location said radiated light passes in a direction through said conduit;

detecting a first portion of said radiated light passing through said fluid conduit and detecting a second portion of said radiated light which is reflected by said exterior surface of said fluid conduit;

comparing said first and second portions of said radiated light with predetermined values therefor whereby:

when said first portion of said radiated light is at a predetermined high level and said second portion of said radiated light is at a predetermined low level, determining that said fluid conduit is not present at said predetermined location.

* * * * *

UNITED STATES PATENT AND TRADEMARK OFFICE
CERTIFICATE OF CORRECTION

PATENT NO. : 6,806,947 B1 Page 1 of 1
DATED : October 19, 2004
INVENTOR(S) : Olof Ekdahl and Per-Ola Wictor It is certified that error appears in the above-identified patent and that said Letters Patent is hereby corrected as shown below:

Column 6,
Line 39, "thismanner" should read -- this manner --.

Column 9,
Line 28, "as" should read -- is --.
Line 62, "are" should read -- is --.

Column 10,
Line 8, "thismanner" should read -- this manner --.

Column 12,
Lines 35-36, "comprising" should read -- comprises --.

Signed and Sealed this

Eighth Day of February, 2005

JON W. DUDAS
*Director of the United States Patent and Trademark Office*